United States Patent
Mautner et al.

[11] Patent Number: 5,910,234
[45] Date of Patent: Jun. 8, 1999

[54] RECOVERY OF ALCOHOLS FROM PROCESS WASTEWATER FROM PRODUCTION OF SILICONE RESIN

[75] Inventors: Konrad Mautner; Erwin Schuhbeck, both of Burghausen, Germany

[73] Assignee: Wacker-Chemie GmbH, Germany

[21] Appl. No.: 08/900,955

[22] Filed: Jul. 25, 1997

[30] Foreign Application Priority Data

Sep. 18, 1996 [DE] Germany ............... 196 38 123

[51] Int. Cl.⁶ ............................................. C02F 1/04
[52] U.S. Cl. ........................ 203/18; 203/37; 203/49; 203/74; 210/718; 210/724; 528/10; 568/913
[58] Field of Search .................... 203/6, 10, 18, 203/37, 49, 74; 210/718, 750, 749, 766, 724; 528/10, 12; 568/913

[56] References Cited

U.S. PATENT DOCUMENTS

| | | | |
|---|---|---|---|
| 3,615,402 | 10/1971 | Rule | 96/15 |
| 3,804,756 | 4/1974 | Callahan et al. | 210/763 |
| 5,198,518 | 3/1993 | Yamamoto et al. | 528/12 |
| 5,246,584 | 9/1993 | Donaldson et al. | 210/603 |
| 5,268,510 | 12/1993 | Schwab et al. | 568/621 |
| 5,378,788 | 1/1995 | Omura et al. | 528/10 |
| 5,562,834 | 10/1996 | Bremer et al. | 210/750 |

FOREIGN PATENT DOCUMENTS

| | | |
|---|---|---|
| 0675128 | 10/1995 | European Pat. Off. . |
| 873433 | 3/1953 | Germany . |
| 2285501 | 10/1985 | Germany . |
| 2285509 | 10/1985 | Germany . |

*Primary Examiner*—Peter A. Hruskoci
*Attorney, Agent, or Firm*—Brooks & Kushman P.C.

[57] ABSTRACT

This invention relates to a process for working up the alcohol-containing wastewater which is obtained in the hydrolysis of silanes of the general formula I $$R^1_a SiCl_b(OR^2)_{4-a-b},\qquad (I)$$

where

R¹ are hydrogen atoms or identical or different monovalent, unsubstituted or halogen-substituted, SiC-bonded $C_1$–$C_{18}$-hydrocarbon radicals, R² are identical or different monovalent $C_1$–$C_{10}$-hydrocarbon radicals, a is 0, 1, 2 or 3, on average from 0.3 to 1.9, and b is 0, 1, 2, 3 or 4, on average from 0.0 to 3.0, with the proviso that the sum a+b is on average at most 3.5, for the preparation of silicone resins, wherein, in the first step, the wastewater is made alkaline by addition of alkali and, in the second step, the alcohol is removed from the resulting alkaline solution or suspension by injection of steam.

11 Claims, No Drawings

RECOVERY OF ALCOHOLS FROM PROCESS WASTEWATER FROM PRODUCTION OF SILICONE RESIN

BRIEF SUMMARY OF THE INVENTION

The present invention relates to a process for working up the alcohol-containing wastewater which is obtained in the hydrolysis of alkoxylated and partially alkoxylated (hydrocarbon)chlorosilanes. The alcohol is separated off in this process.

BACKGROUND OF THE INVENTION

Silicone resins comprise three-dimensional networks which are made up of trifunctional or tetrafunctional silicon units $R^1SiO_{3/2}$ or $SiO_{4/2}$, where $R^1$ is selected from the group consisting of aliphatic or aromatic hydrocarbon radicals. In addition, linear units $R^1{}_2SiO$ and/or monofunctional units $R^1{}_3SiO_{1/2}$ may also be present The hydrolysis of trifunctional chlorosilanes or silicon tetrachloride with water leads to a high proportion of gel in the hydrolysate, even when the hydrolysis is carried out in the presence of organic solvents such as toluene and acetone.

The preparation of resin from partially alkoxylated chlorosilanes or alkoxysilanes described in DE-A873 433, in which the formation of gel is greatly reduced, was introduced a long time ago. The hydrolysis results in the resin product plus an alcohol-containing aqueous phase comprising the hydrochloric acid formed from the chlorosilanes as well as residues of silicone resin and amounts of gel.

In order to make resin production economical and to avoid waste, it is of great interest to recover the alcohol used from the aqueous phase simply and as completely as possible. The greatest problem in the work-up of this process stream is posed by the amounts of resin and gel. If the alcohol is distilled from the mixture in a pot still or distillation column, deposits of accumulating silicone resin are formed on the heat exchangers after a short time and these hinder heat transfer and have to be removed periodically. Even when steam is injected directly, deposits on the walls are formed from the amounts of gel under acid conditions.

A further problem in the work-up of the aqueous-alcoholic phase is in many cases the acid which is necessary as condensation catalyst. Since hydrochloric acid which is formed in the hydrolysis of the partially alkoxylated silanes is frequently used, readily volatile alkyl halides are formed from the alcohols and HCl on heating and these in turn cause emission problems.

Steam stripping of organic-containing wastewater is used to remove volatile organic constituents. Hwang, Y.-L. et al.; Ind. Eng. Chem. Res. 1992, 31, 1753–1759 and Hwang Y.-L. et al.; Ind. Eng. Chem. Res. 1992, 31, 1759–1768 give the necessary criterion for successfully carrying out steam stripping of wastewater as a vapor-liquid equilibrium constant at infinite dilution $K^\infty>1$. Alcohols have low $K^\infty$ values, e.g. ethanol –0.4 and methanol –0.5. Hassan, S. Q.; J. Air Waste Manage. Assoc., 1992, 42, 936–943 gives the criterion for successfully carrying out steam stripping as a solubility of the organic constituent in water of at most 1000 ppm. Steam stripping is accordingly completely unsuitable for removing alcohols such as ethanol or methanol from an aqueous solution.

DD-A-228 550 describes the recovery of alcohol from the aqueous-alcoholic hydrochloric acid which is obtained in the preparation of methylsilicone resins by passing in steam, however, it does not describe how the process is carried out and how gel deposits occurring in the hydrochloric acid medium and the alkyl chloride emissions can be avoided.

DETAILED DESCRIPTION OF THE INVENTION

It is an object of the present invention to recover the alcohol from process wastewater from the preparation of silicone resin, to drastically lower the emissions of alkyl halides and to suppress the deposit formation on apparatus components.

The present invention provides a process for working up the alcohol-containing wastewater which is obtained in the hydrolysis of silanes of the formula $$R^1{}_aSiCl_b(OR^2)_{4-a-b} \tag{I}$$

where
  $R^1$ is a hydrogen atom or identical or different monovalent, unsubstituted or halogen-substituted, SiC-bonded $C_1$–$C_{18}$ -hydrocarbon radicals,
  $R^2$ is an identical or different monovalent $C_1$–$C_{10}$-hydrocarbon radicals,
  a is 0, 1, 2 or 3, on average from 0.3 to 1.9, and
  b is 0, 1, 2, 3 or 4, on average from 0.0 to 3.0,
with the proviso that the sum a+b is on average at most 3.5, for the preparation of silicone resins, where,
in a first step,
the wastewater is made alkaline by addition of alkali and,
in a second step,
the alcohol is removed from the resulting alkaline wastewater by injection of steam.

Example of radicals $R^1$ are alkyl radicals such as the methyl ethyl, n-propyl, iso-propyl, n-butyl, iso-butyl tert-butyl, n-pentyl, iso-pentyl, neo-pentyl, tert-pentyl radicals, hexyl radicals such as the n-hexyl radical, heptyl radicals such as the n-heptyl radical, octyl radicals such as the n-octyl radical and iso-octyl radicals such as the 2,2,4-trimethylpentyl radical, nonyl radicals such as the n-nonyl radical, decyl radicals such as the n-decyl radical, dodecyl radicals such as the n-dodecyl radical, octadecyl radicals such as the n-octadecyl radical; alkenyl radicals such as the vinyl and allyl radicals; cycloalkyl radicals such as cyclopentyl, cyclohexyl, cycloheptyl and methylcyclohexyl radicals; aryl radicals such as the phenyl, naphthyl, anthryl and phenanthryl radicals; alkalyl radicals such as o-, m-, p-tolyl radicals, xylyl radicals and ethylphenyl radicals; aralkyl radicals such as the benzyl radical, the alpha- and b-phenylethyl radicals.

Examples of halogen-substituted radicals $R^1$ are haloalkyl radicals such as the 3,3,3-trifluoro-n-propyl radical, the 2,2,2,2',2',2'-hexafluoroisopropyl radical, the heptafluoroisopropyl radical, and haloaryl radicals such as o-, m- and p-chlorophenyl radicals.

Preferred radicals $R^1$ are unsubstituted $C_1$–$C_6$-hydrocarbon radicals, in particular the methyl and phenyl radicals.
where
  $R^1$ is a hydrogen atom or identical or different monovalent, unsubstituted or halogen-substituted, SiC-bonded $C_1$–$C_{18}$-hydrocarbon radicals,
  $R^2$ is an identical or different monovalent $C_1$–$C_{10}$-hydrocarbon radicals,
  a is 0, 1, 2 or 3, on average from 0.3 to 1.9, and
  b is 0, 1, 2, 3 or 4, on average from 0.0 to 3.0,
with the proviso that the sum a+b is on average at most 3.5, for the preparation of silicone resins, where,
in a first step,
the wastewater is made alkaline by addition of alkali and,
in a second step,
the alcohol is removed from the resulting alkaline wastewater by injection of steam.

Example of radicals $R^1$ are alkyl radicals such as the methyl, ethyl n-propyl, iso-propyl, n-butyl, iso-butyl, tert-butyl, n-pentyl, iso-pentyl, neo-pentyl, tert-pentyl radicals, hexyl radicals such as the n-hexyl radical, heptyl radicals such as the n-heptyl radical, octyl radicals such as the n-octyl radical and iso-octyl radicals such as the 2,2,4-trimethylpentyl radical, nonyl radicals such as the n-nonyl radical, decyl radicals such as the n-decyl radical, dodecyl radicals such as the n-dodecyl radical, octadecyl radicals such as the n-ocadecyl radical; alkenyl radicals such as the vinyl and allyl radicals; cycloalkyl radicals such as cyclopentyl, cyclohexyl, cycloheptyl and methylcyclohexyl radicals; aryl radicals such as the phenyl, naphthyl, anthryl and phenanthryl radicals; alkaryl radicals such as o-, m-, p-tolyl radicals, xylyl radicals and ethylphenyl radicals; aralkyl radicals such as the benzyl radical, the alpha- and b-phenylethyl radicals.

Examples of halogen-substituted radicals $R^1$ are haloalkyl radicals such as the 3,3,3-trifluoro-n-propyl radical, the 2,2,2,2',2',2'-hexafluoroisopropyl radical, the heptafluoroisopropyl radical, and haloaryl radicals such as o-, m- and p-chlorophenyl radicals.

Peferred radicals $R^1$ are unsubstituted $C_1$–$C_6$-hydrocarbon radicals, in particular the methyl and phenyl radicals.

Examples of hydrocarbon radicals $R^2$ having 1–10 carbon atoms are given above in the examples of $R^1$. The radicals R2 are preferably linear or branched $C_1$–$C_4$-hydrocarbon radicals, in particular methyl and/or ethyl radicals.

The alcohol content of the alcohol-containig wastewater from the hydrolysis (process wastewater) can vary greatly and is generally from 5% to 50% by weight. In the preferred case for ethanol, the content is from 15% to 45% by weight.

The silanes of formula I can be partially or fully alkoxylated, i.e. they can contain chlorine atoms. A proportion of at most 10% by weight, preferably at most 2% by weight, of the silanes of formula I can contain only chlorine atoms but no groups $OR^2$.

Apart from the alcohol which has been liberated from the silanes, the aqueous phase may additionally comprise catalyst used for the hydrolysis and condensation. This is generally an acid, in the simplest case hydrochloric acid if chlorine-containing silanes have been used for the hydrolysis. In this case, the value of b is on average at least 0.2, preferably at least on average 0.5. Like the alcohol content, the acid content can also vary greatly from 2% to 20% by weight depending on the type of resin. For the preferred preparation process for resins from partially alkoxylated chlorosilanes, the acid concentration is between 10% and 20% by weight.

The deposits on apparatus components are caused by the silicone resin present in the process wastewater, if the process of the invention is not used. This is present in the water, for example, in the form of emulsified droplets or as a dispersed, gel-like, voluminous, greasy mass. The amount is in turn dependent on the type of resin. The amount of gel generally rises with the proportion of trifunctional or tetrafunctional silanes. In the extreme case, the amount of gel can be up to 5% by volume of the process wastewater.

If the preparation of resin is carried out in the presence of solvents, traces thereof are present in the aqueous phase and in the gel. It is possible to use solvents which have large micscibility gaps with water under normal conditions, e.g. aliphatic and aromatic hydrocarbons in the boiling range up to 250° C. or esters and ketones having more than 3 carbon atoms. Preference is given to using aromatic hydrocarbons, more preferably toluene and xylene.

Further components present in the process wastewater can be denaturants from the alcohol which has been used for the conversion of the (hydrocarbon)chlorosilanes into the silanes of formula I; impurities which have been introduced via the startng materials, e.g. saturated or unsaturated hydrocarbons from the (hydrocarbon)chlorosilanes; and alkyl halides which can form during the alkoxylation or hydrolysis from olefins by addition or from the alcohols by substitution reactions with hydrohalic acids. The proportion of these further components present in the wastewater is preferably at most 1% by weight.

In the first step, alkali is added to the above-described process waste water. It is possible to use both organic and inorganic bases in pure form or in the form of an aqueous solution. Preference is given to using aqueous solutions of alkali metal hydroxides, in particular sodium hydroxide solution. The concentration of alkali metal hydroxide is preferably 20% –50% by weight.

The addition of alkali is preferably carried out continuously at temperatures of from 0° C. to 40° C., in particular from 10° C. to 30° C., and preferably at from 0.05 MPa to 1 MPa. However, different temperatures and pressures or discontinuous addition are not ruled out. The amount added is such that the pH of the mixture is at least 8, preferably from 11 to 13.

The addition of alkali causes extremely rapid condensation of the resin and gel droplets to give insoluble organosilicic acid. This organosilicic acid is very low in residual groups and has only a low surface energy. It therefore no longer deposits on surfaces and can easily be filtered off in the form of fine particles.

In contrast, the condensation in an acid medium proceeds more slowly and resins which are high in residual groups are formed; these slowly grow on all available surfaces and form deposits, so that cleaning has to be carried out periodically. Therefore, in an acid work-up, it has to be ensured that the amounts of gel in the process wastewater are minimized, which can be achieved, for example, by additional separation devices. This additional outlay is unnecessary in an alkaline work-up.

The second important effect of the alkali is the minimization of alcohol losses via a substitution reaction with the hydrohalic acids which are used, resulting in alkyl halides which in turn represent a significant emission problem.

The second step is steam stripping. For this purpose, the alkaline mixture from the first step is fed to a column. This is advantageously a bubble column without additional internal fittings in order to avoid formation of deposits of resin particles. At the same time, steam is fed in. The feed into the column can be either in cocurrent or in countercurrent. Preference is given to countercurrent feed with the steam being fed in at the bottom and the alkaline mixture being introduced in the upper half of the column. The ratio of steam to alkaline mixture is dependent on the alcohol content of the mixture and on the energy content of the steam used, and it is therefore only possible to give examples of this ratio (see Examples).

The mixture of alcohol and water which is vaporized in the second step is preferably condensed and is both neutral and free of solids and gels. Only solvents present in the process wastewater can still be present. The ratio of alcohol:water can vary greatly depending on the conditions in the steam stripping, however, it is advantageously at least 1:2, preferably at least 1:1.

The residual alcohol content of the liquid taken from the bubble column is usually less than 1% by weight.

The alcohol/water mixture separated off in the process can be used directly in resin production, if the process is carried out appropriately.

The alcohol separated off is freed completely or partially of residual water. The alcohol is concentrated, e.g. by distillation or by separation using a membrane process, to a content of 90% –100% by weight and then reused in resin production.

In the following examples, unless otherwise indicated,
a) all amounts are by weight;
b) all pressures are 0.10 MPa (abs.);
c) all temperatues are 20° C.

EXAMPLES:

The examples were carried out using a process wastewater from methyl-silicone resin production having the following composition:

| Component | Proportion [% by weight] | Mass flow [kg/h] |
| --- | --- | --- |
| Water | 68.3 | 2.05 |
| Ethanol | 21 | 0.63 |
| HCl | 10 | 0.3 |
| Toluene | 0.1 | 0 |
| Resin/gel | 0.5 | 0.02 |
| Ethyl chloride | 0.1 | 0 |

EXAMPLE 1

The process wastewater was adjusted to a pH of 12 using aqueous NaOH (25% by weight). A bubble column (Æ100 mm, length 2000 mm, Duran glass) was 60%-filled with the process wastewater. The process wastewater was metered in by means of a diaphragm pump at the level of the liquid surface. At the bottom, the process wastewater depleted in alcohol was taken off by means of a diaphragm pump. 100 mm above the bottom offtake, steam having a temperature of 160° C. was fed in through a nozzle. The ratio steam:process waste-water was 0.9. The metering rate of the process wastewater was 3 kg/h.

The distillate consisted of:

| Component | Proportion [% by weight] | Mass flow [kg/h] |
| --- | --- | --- |
| Water | 29.3 | 0.22 |
| Ethanol | 69.9 | 0.53 |
| Toluene | 0.4 | 0 |
| Ethyl chloride | 0.4 | 0 |

The liquid taken off at the bottom contained fine methylsilicic acid particles and 0.8% by weight of ethanol. The glass column had no deposits after 100 hours.

Only the amount of ethyl chloride which was originally present was found; no new formation took place.

EXAMPLE 2 (COMPARATIVE EXAMPLE)

Example 1 was repeated but the process wastewater was not pretreated. After only a few hours, a coating started to form on the glass. At the end of the experiment after 100 hours, the cross section of the bottom offtake line had been almost halved by deposit formation and the line had to be cleaned. The liquid taken off at the bottom contained a few methylsilicic acid particles of irregular size which had flaked off from wall deposits and 0.9% by weight of ethanol.

The distillate consisted of:

| Component | Proportion [% by weight] | Mass flow [kg/h] |
| --- | --- | --- |
| Water | 29.3 | 0.22 |
| Ethanol | 69.1 | 0.52 |
| Toluene | 0.4 | 0 |
| Ethyl chloride | 1.2 | 0.01 |

New formation of ethyl chloride took place.

What is claimed is:

1. A process for recovering alcohol from the alcohol-containing wastewater containing resin droplets and/or gel which is obtained in the hydrolysis of silanes of the formula $$R^1_a SiCl_b (OR^2)_{4-a-b},\qquad\mathrm{(I)}$$

where

R$^1$ is a hydrogen atom or identical or different monovalent, unsubstituted or halogen-substituted, SiC-bonded C$_1$–C$_{18}$-hydrocarbon radicals, R$^2$ is an identical or different monovalent C$_1$–C$_{10}$-hydrocarbon radical, a is 0, 1, 2 or 3, on average from 0.3 to 1.9, and b is 0, 1, 2, 3 or 4, on average from 0.0 to 3.0, with the proviso that the sum a+b is on average at most 3.5, for the preparation of silicone resins, wherein, in the first step, the wastewater is made alkaline by addition of alkali to condense said resin droplets and/or gel into insoluble organosilicic acid and, in the second step, the alcohol is removed from the resulting alkaline wastewater by injection of steam.

2. The process as claimed in claim 1, wherein R$^1$ is a methyl or phenyl radical.

3. The process as claimed in claim 1, wherein R$^2$ is a methyl or ethyl radical.

4. The process as claimed in claim 1, wherein the alcohol content of the alcohol-containing wastewater from the hydrolysis is from 5% to 50% by weight.

5. The process as claimed in claim 1, wherein, in the first step, the alkali used is an aqueous solution of an alkali metal hydroxide.

6. The process as claimed in claim 1, wherein, in the first step, the pH of the wastewater is adjusted to at least 8 by addition of the alkali.

7. A process for recovering alcohol from alcohol-containing wastewater obtained by the hydrolysis of alkoxy-functional silanes, the wastewater containing resin droplets and/or gel, and less than 5 percent by weight of organosilane compounds, said process comprising:

adding a basic substance to the wastewater to render it alkaline to condense said resin droplets and/or gel into insoluble organosilicic acid; and removing alcohol from the alkaline wastewater by injecting steam.

8. The process of claim 7 wherein the pH of the wastewater is between 11 and 13.

9. The process of claim 7 wherein said basic substance comprises an alkali metal hydroxide.

10. The process of claim 7 further comprising the step of recovering an alcohol enriched distillate.

11. The process of claim 10 wherein said alcohol enriched distillate is distilled to recover a distillate consisting essentially of alcohol.

* * * * *